United States Patent [19]

Alder et al.

[11] Patent Number: 5,106,872

[45] Date of Patent: Apr. 21, 1992

[54] PESTICIDAL COMPOSITIONS WITH ENHANCED ACTIVITY

[75] Inventors: Alex Alder, Arisdorf; Alfred Rindlisbacher, Muttenz; Hans-Peter Streibert, Magden; Rudolf Bänninger, Ettingen, all of Switzerland

[73] Assignee: Ciba-Geigy Corporation, Ardsley, N.Y.

[21] Appl. No.: 499,126

[22] Filed: Mar. 26, 1990

[30] Foreign Application Priority Data

Mar. 31, 1989 [CH]  Switzerland .......................... 1182/89

[51] Int. Cl.[5] ...................... A01N 43/10; A01N 47/28
[52] U.S. Cl. .................................. 514/587; 514/454; 514/586
[58] Field of Search .................. 514/454, 587, 586

[56] References Cited

U.S. PATENT DOCUMENTS

| | | | |
|---|---|---|---|
| 3,395,233 | 7/1968 | Duerr et al. | 424/322 |
| 3,950,265 | 4/1976 | Albrecht et al. | 252/311 |
| 4,194,008 | 3/1980 | Enders et al. | 424/322 |
| 4,328,247 | 5/1982 | Drabek et al. | 424/326 |
| 4,404,225 | 9/1983 | Boger et al. | 424/322 |
| 4,520,072 | 5/1985 | Yoshino et al. | 428/403 |
| 4,647,578 | 3/1987 | Crounse et al. | 514/454 |

FOREIGN PATENT DOCUMENTS 0146059  6/1985  European Pat. Off. .

OTHER PUBLICATIONS

Derwent Abstract No. 73-69534U/46 of French Pat. No. 2,168,186.
Brighton Crop Protection Conference 1, 1988, pp. 25–32 (Streibert et al).

*Primary Examiner*—Allen J. Robinson
*Attorney, Agent, or Firm*—Edward McC. Roberts

[57] ABSTRACT

The insecticidal and acaricidal activity of N-phenylthioureas can be enhanced and prolonged by the simultaneous application of photosensitizers, and this activity can also be effected within a shorter period of time after application.

13 Claims, No Drawings

PESTICIDAL COMPOSITIONS WITH ENHANCED ACTIVITY

The present invention relates to methods of enhancing the activity of insectidical and acaricidal N-phenylthioureas by the addition of photosensitisers. The invention further relates to pesticidal compositions which contain an insecticidally and acaricidally active N-phenylthiourea and a photosensitiser.

Acaricides and insecticides of the class of the N-phenylureas, the pesticidal activity of which can be enhanced by the process of this invention, are described in the literature. Such pesticidal compounds are disclosed, for example, in U.S. Pat. Nos. 3,395,233 or 4,404,225European patent application 298 915 or in German Offenlegungsschrift specifications 2 639 748 or 3 034 905. In particular, the compounds disclosed in German Offenlegungsschrift 3 034 905 have proved in practice to be highly effective acaricides and insecticides against spider mites and insects that damage plants. When using these pesticides against plant pests, it has been found that the onset of the desired action against noxious insects and mites is observed only after a certain lapse of time following application and that the action diminishes after a certain time, thus making it necessary to carry out a number of treatments within a crop period.

It is therefore the object of the present invention to shorten the time between application of the pesticide and the onset of pesticidal activity, to prolong the duration of activity of the applied pesticide, and to reduce the application rate of said pesticide.

The invention therefore postulates effecting a more rapid onset of the insecticidal and acaricidal action of N-phenylthioureas and to prolong said action by applying the N-phenylthiourea together with a photosensitiser.

A preferred embodiment of the present invention comprises enhancing the activity of those pesticidal compounds which fall under formula I

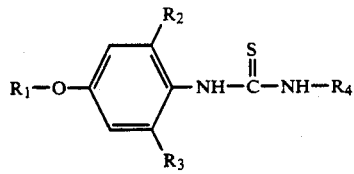

wherein
$R_1$ is phenyl, pyridyl, or phenyl or pyridyl each substituted by one or substituents selected from the group consisting of $C_1$-$C_4$alkyl, trifluormethyl or nitro,
$R_2$ and $R_3$ are each independently of the other $C_1$-$C_4$alkyl, and
$R_4$ is $C_1$-$C_{10}$alkyl, $C_3$-$C_5$alkenyl, $C_3$-$C_6$cycloalkyl or $C_3$-$C_6$cycloalkyl-$C_1$-$C_4$alkyl,
by adding photosensitisers thereto.

Suitable photosensitisers are typically aromatic carbonyl compounds and/or different organic dyes. Illustrative examples of such sensitisers are compounds of the classes of the xanthene dyes (for example Rose Bengal), thiazines (for example Methylene Blue), porphyrins (for example tetraphenylporphyrin), thionines, eosines, erythrosines, phenosafranines, chlorophylls, flavines, thioxanthones, phthalocyanines, thiophenes, naphthalene derivatives, phenothiazines, pyrazolanthrones, ketocoumarins, azines (for example riboflavine), anthraquinones, metallocenes, benzophenones and anthracene derivatives. Photosensitisers which have proved especially suitable for use in the practice of this invention are those which are described in the literature as singlet oxygen sensitisers. Among these sensitisers, the xanthene dyes, thioxanthones, anthraquinones and phthalocyanines have proved particularly useful in conjunction with the compounds of formula I above. Particularly preferred individual compounds of these classes are: disodium salt of 3',4',5',6'-tetrachloro-2,4,5,7-tetraiodofluoroescein (Rose Bengal) of formula II

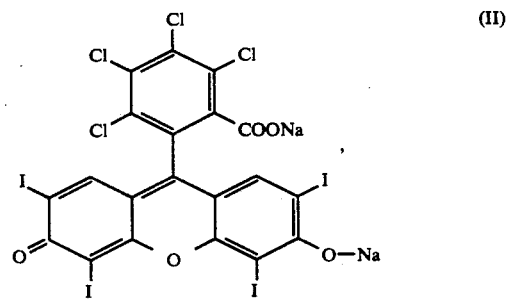

aluminium phthalocyaninesulfonic acid, sodium salt, of formula III

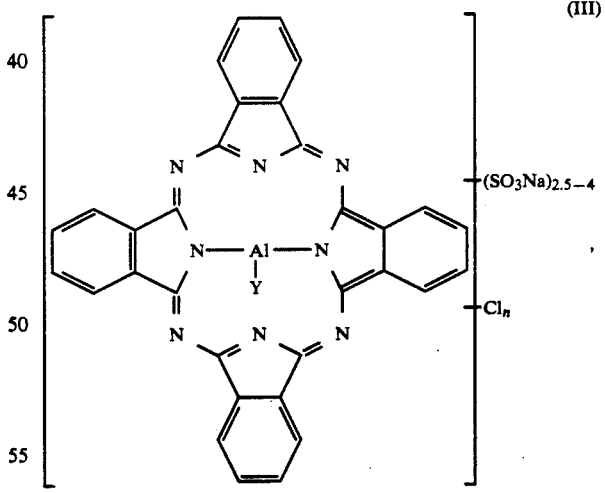

having a degree of sulfonation of 2.5 to 4, wherein n is 0 or 1 and Y is hydroxy or halogen. Preferred compounds of formula III are those in which Y is hydroxy. These compounds will be referred to hereinafter as compound 3a (Y=OH, n=0 or 1=and compound 3b (Y=Cl, n=0 or 1);

1-amino-4-bromoanthraquinone-2-sulfonic acid, sodium salt, of formula IV

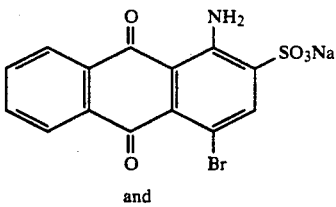

(IV)

and nonaethylene glycol thioxanthone-1-carboxylate of formula V

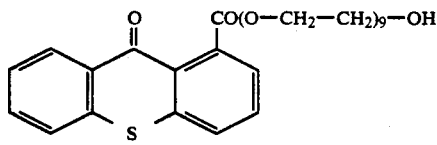

(V)

The definitions of the substituents of formula I encompass a narrow selection of known insecticides and acaricides of the class of the N-phenylthioureas. The definitions of the substituents typically denote the following radicals:

halogen is fluoro, chloro, bromo or iodo, preferably fluoro or chloro, $C_1$–$C_4$alkyl is methyl, ethyl, n-propyl, isopropyl, n-butyl, sec-butyl, isobutyl or tert-butyl, pyridyl, depending on the site of attachment to the linking oxygen atom, is 2-pyridyl, 3-pyridyl or 4-pyridyl, substituted pyridyl is typically halopyridyl, dihalopyridyl, trifluoromethylpyridyl, halotrifluoromethylpyridyl such as 3,5-dichloropyridyl, 5-chloro-3-fluoropyridyl, 5-trifluoromethylpyridyl, 3-chloro-5-trifluoromethylpyridyl and the like, substituted phenyl is typically halophenyl, alkylphenyl, dihalophenyl, trifluoromethylphenyl and the like, $C_1$–$C_{10}$alkyl denotes isomeric straight-chain and branched alkyl chains which are possible in accordance with the indicated number of carbon atoms, $R_4$ preferably denoting branched alkyl radicals, $C_3$–$C_6$alkenyl is allyl, methallyl, 2-butenyl, 3-butenyl and isomeric 2- and 3-pentenyl, $C_3$–$C_6$cycloalkyl is preferably cyclopropyl or cyclohexyl, cycloalkylalkyl is preferably cyclopropylethyl or cyclohexylethyl, most preferably 1-cyclopropylethyl.

The compounds listed in the following Table 1 are illustrative of those which fall under formula I.

TABLE 1

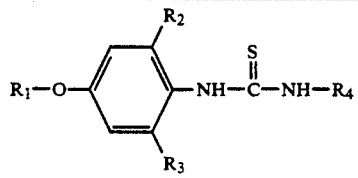

| Comp. | $R_1$ | $R_2$ | $R_3$ | $R_4$ | Phys. data |
|---|---|---|---|---|---|
| 1a | $C_6H_5$ | $C_3H_7$-i | $C_3H_7$-i | $C_4H_9$-t | m.p. 149.6° C. |
| 1b | 4-Cl—$C_6H_4$— | $C_3H_7$-i | $C_3H_7$-i | $C_4H_9$-t | m.p. 146–148° C. |
| 1c | 3-CF$_3$—$C_6H_4$— | $C_3H_7$-i | $C_3H_7$-i | $C_4H_9$-t | m.p. 83–85° C. |
| 1d | 4-Cl—$C_6H_4$— | $C_2H_5$ | $C_4H_9$-s | $C_4H_9$-t | m.p. 91–92° C. |
| 1e | 4-Cl—$C_6H_4$— | $C_2H_5$ | $C_3H_7$-i | $C_4H_9$-t | m.p. 127–129° C. |
| 1f | 4-CH$_3$—$C_6H_4$— | $C_3H_7$-i | $C_3H_7$-i | $C_4H_9$-t | m.p. 168–170° C. |
| 1g | 4-CH$_3$—$C_6H_4$— | $C_3H_7$-i | $C_3H_7$-i | $C_3H_7$-i | m.p. 146–147° C. |
| 1h | $C_6H_5$ | $C_3H_7$-i | $C_3H_7$-i | $CH_3$ | m.p. 130–131° C. |
| 1i | $C_6H_5$ | $C_3H_7$-i | $C_3H_7$-i | $C_2H_5$ | m.p. 148–149° C. |
| 1j | $C_6H_5$ | $C_3H_7$-i | $C_3H_7$-i | $C_3H_7$-n | m.p. 121–122° C. |
| 1k | $C_6H_5$ | $C_3H_7$-i | $C_3H_7$-i | $C_3H_7$-i | m.p. 160–161° C. |
| 1l | $C_6H_5$ | $C_3H_7$-i | $C_3H_7$-i | $C_4H_9$-n | m.p. 117–119° C. |
| 1m | $C_6H_5$ | $C_3H_7$-i | $C_3H_7$-i | $C_4H_9$-i | m.p. 152–153° C. |
| 1n | $C_6H_5$ | $C_3H_7$-i | $C_3H_7$-i | $C_4H_9$-s | m.p. 157–158° C. |
| 1o | $C_6H_5$ | $C_3H_7$-i | $C_3H_7$-i | $C_5H_{11}$-n | m.p. 121–122° C. |
| 1p | 4-CH$_3$—$C_6H_4$— | $C_3H_7$-i | $C_3H_7$-i | $C_4H_9$-s | m.p. 156–157° C. |
| 1q | 4-Cl—$C_6H_4$— | $C_3H_7$-i | $C_3H_7$-i | $C_3H_5$-cycl. | m.p. 143–145° C. |
| 1r | 4-Cl—$C_6H_4$— | $C_2H_5$ | $C_3H_7$-i | $C_3H_5$-cycl. | m.p. 80–95° C. |
| 1s | 4-Cl—$C_6H_4$— | $C_2H_5$ | $C_4H_9$-s | $CH_3$ | m.p. 109–110° C. |
| 1t | $C_6H_5$ | $C_2H_5$ | $C_4H_9$-s | $C_3H_7$-i | m.p. 107–110° C. |
| 1u | $C_6H_5$ | $C_2H_5$ | $C_4H_9$-s | $C_4H_9$-t | m.p. 97–100° C. |
| 1v | 3-Cl-4-Cl—$C_6H_3$— | $C_3H_7$-i | $C_3H_7$-i | $C_4H_9$-t | |
| 1w | $C_6H_5$ | $C_3H_7$-i | $C_3H_7$-i | $C_{10}H_{21}$-n | |
| 1x | $C_6H_5$ | $C_3H_7$-i | $C_3H_7$-i | $C_7H_{15}$-n | |
| 1y | 4-NO$_2$—$C_6H_4$— | $C_3H_7$-i | $C_3H_7$-i | $C_4H_9$-t | |
| 1z | 4-CF$_3$—$C_6H_4$— | $C_3H_7$-i | $C_3H_7$-i | $C_4H_9$-t | |
| 1aa | 4-Cl-5-Cl-pyrid-2-yl | $C_2H_5$ | $C_2H_5$ | $C_4H_9$-t | m.p. 140° C.(dec.) |
| 1bb | 4-Cl-5-Cl-pyrid-2-yl | $C_3H_9$-i | $C_3H_7$-i | $C_4H_9$-t | m.p. 154° C.(dec.) |
| 1cc | 4-Cl-5-Cl-pyrid-2-yl | $C_3H_9$-i | $C_3H_7$-i | $C_3H_7$-i | m.p. 167–169° C. |
| 1dd | 4-Cl-5-Cl-pyrid-2-yl | $C_3H_9$-i | $C_3H_7$-i | $C_5H_9$-cycl. | m.p. 172–174° C. |
| 1ee | 4-Cl-5-Cl-pyrid-2-yl | $C_3H_9$-i | $C_3H_7$-i | $C_4H_9$-s | m.p. 134–136° C. |
| 1ff | 4-Cl-5-Cl-pyrid-2-yl | $C_3H_9$-i | $C_3H_7$-i | $C(CH_3)$—$C_2H_5$ | m.p. 142–143° C. |
| 1gg | 4-Cl-5-Cl-pyrid-2-yl | $C_3H_9$-i | $C_3H_7$-i | $CH_3$ | m.p. 127–129° C. |
| 1hh | 4-Cl-5-Cl-pyrid-2-yl | $CH_3$ | $CH_3$ | $C_4H_9$-t | m.p. 147° C.(dec.) |
| 1ii | 4-Cl-5-Cl-pyrid-2-yl | $C_2H_5$ | $C_4H_9$-s | $C_4H_9$-t | m.p. 127–129° C. |
| 1jj | 4-Cl-5-Cl-pyrid-2-yl | $C_3H_7$-i | $C_3H_7$-i | $C_3H_5$-cycl. | m.p. 147–150° C. |
| 1kk | 4-Cl-5-Cl-pyrid-2-yl | $C_3H_7$-i | $C_3H_7$-i | $C_6H_{11}$-cycl. | m.p. 174–177° C. |
| 1ll | 4-Cl-5-Cl-pyrid-2-yl | $C_3H_7$-i | $C_3H_7$-i | $CH(CH_3)$—$C_4H_9$-i | m.p. 131–133° C. |
| 1mm | 4-Cl-5-Cl-pyrid-2-yl | $C_3H_7$-i | $C_3H_7$-i | $CH(CH_3)$—$C_3H_5$-cycl. | m.p. 138–140° C. |

TABLE 1-continued

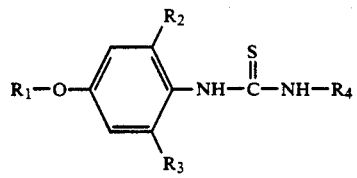

| Comp. | R₁ | R₂ | R₃ | R₄ | Phys. data |
|---|---|---|---|---|---|
| 1nn | 4-F-5-Cl-pyrid-2-yl | $C_3H_7$-i | $C_3H_7$-i | $C_4H_9$-t | m.p. 115–116° C. |

Preferred compounds of formula I the pesticidal activity of which can be enhanced are those wherein $R_1$ is phenyl or phenyl which is monosubstituted by halogen, $C_1$–$C_4$alkyl or trifluoromethyl, and $R_4$ is $C_1$–$C_4$alkyl. The preferred individual compound is N-(2,6-diisopropyl-4-phenoxyphenyl)-N'-tert-butylthiourea (compound 1a).

A preferred embodiment of the process of this invention substantially comprises applying the compound of formula I and the photosensitiser of formula II, III, IV or V at the same locus, generally to the cultivated area or cultivated plant. These two components can be applied jointly and simultaneously, or in succession, to the locus. For economic reasons, the compound of formula I and the photosensitiser are usually applied simultaneously, either as tank mixture consisting of pesticide dispersion of formula I and photosensitiser, or in the form of a jointly formulated composition, to the desired locus. As the compounds of formula I are preferably used for controlling insects and acarids that damage plants, the process of this invention will be applied with advantage to the treated cultivated plants such as cotton, ornamentals, fruit, citrus or vegetables. Application is made in conventional manner by spraying the pesticides in the form of an aqueous suspension of the desired concentration to the treated cultivated plants.

The rates of concentration, based on the pesticidal compounds of the class of the N-phenylthioureas, are in the process of this invention from 0.1 to 1000 ppm, preferably from 5 to 5000 ppm, most preferably from 10 to 400 ppm. The photosensitiser is added to the suspension containing the pesticidal N-phenylthiourea in concentrations in the range from 0.01 to 50 mol %, based on the amount of pesticide. The amount of photosensitiser added is preferably from 0.1 to 10 mol %, most preferably from 1 to 5 mol %. The concentration of pesticide for controlling pests on cultivated plants is from 0.1 to 1000 g/ha, preferably from 5 to 500 g/ha and, most preferably, from 10 to 400 g/ha.

The addition of a photosensitiser to the pesticides of the class of the N-phenylthioureas effects an enhancement of activity in three respects, as compared with the use of thioureas by themselves.

Firstly, a more rapid onset of pesticidal action after application is achieved, i.e. the time between the application of the pesticide and the onset of pesticidal action is markedly reduced by the addition of a photosensitiser. Secondly, a prologation of the duration of pesticidal action after application is observed, so that the number of times the cultivated plants require to be treated during a vegetation period can be reduced. Thirdly, an enhancement of pesticidal action when using low concentrations of pesticide is observed. Thus the addition of a photosensitiser enhances activity against the pests, even when using low concentrations of pesticide at which this latter by itself would permit only partial control of infestation.

These activity-enhancing and activity-prolonging effects occur in addition to the reduction of the time until the onset of action when applying the teaching of this invention. They permit, however, a reduction of the concentration of insecticide and acaricide while simultaneously prolonging activity—a feature which is considered desirable from the environmental and economic points of view.

The addition of photosensitiser has been found particularly advantageous when the pesticidal compound of the class of N-phenylthioureas is formulated as a wettable powder or as a flowable formulation. The characteristic feature of these formulations is that they contain undissolved pesticide and, as the case may be, of solid water-insoluble carriers. In the process of this invention, pesticidal suspensions are prepared with advantage from water dispersible powders or suspension concentrates of the finely ground pesticide of the class of the N-phenylthioureas, in which suspensions the average granular size of the pesticide is from 2 μm to 8 μm, preferably from 2 μm to 5 μm. Such dispersions are obtained by grinding the pesticide to the desired granular size and then formulating them with suitable formulation assistants such as carriers and/or surface-active agents. Ready for use wettable powders and suspension concentrates suitable for dilution with water contain from 1 to 75% by weight of pesticide. These concentrates are diluted for application with water to the desired spray mixture concentration. The desired amount of photosensitiser can then be added to these suspensions to give so-called tank mixtures.

Owing to the particularly good biological activity achieved, the combination of compound 1a with a photosensitiser of formula II or III is to be singled out as preferred pesticidal combination for carrying out the process of this invention.

So far the best biological results have been obtained with the process of this invention by applying N-(2,6-diisopropyl-4-phenoxyphenyl)-N'-tert-butylthiourea in the form of a wettable powder suspended in water or suspension concentrate which contains the pesticide in an average particle size from 2 μm to 8 μm, and to which 3',4',5',6'-tetrachloro-2,4,5,7-tetraiodofluorescein, disodium salt, or the sodium salt of hydroxyaluminiumphthalocyaninesulfonic acid (compound 3a) is added as sensitiser in an amount of 0.1 to 10 mol %, based on the amount of the active thiourea.

To increase the safety of application it is desirable to provide the pesticidally active N-phenylthiourea and the eligible photosensitiser in a joint formulation for the end user, so that a ready for use spray mixture may be obtained from such a formulation by simple dispersion in water. Compositions which contain the pesticide of the class of the N-phenylthioureas and a photosensitiser constitute an object of the present invention.

Insecticidal and acaricidal compositions of this invention having enhanced activity contain, in addition to a suitable water-insoluble carrier and/or adjuvant, one the one hand an insecticidally and acaricidally active N-phenylthiourea as pesticide and, on the other, a photosensitiser.

Normally in such compositions the sum of the N-phenylthiourea component and of the photosensitiser component will altogether not be more that 75% by weight. The amount of photosensitiser will usually be 0.01 to 50 mol %, based on the amount of pesticide. Commercial compositions of this invention will generally contain not less than 1% by weight of the combination of pesticide and photosensitiser, and are in the form of wettable formulations or flowable formulations. The granular size of the mixture of pesticide and photosensitiser will normally be reduced to an average diameter of 2 $\mu$m to 8 $\mu$m, preferably 2 $\mu$m to 5 $\mu$m, by grinding these substances in a suitable mill before the addition of formulation assistants such as water-insoluble carrier and surface-active agent.

Compositions of this invention having improved activity are prepared by methods conventionally employed in the art of formulation either by homogenising a mixture of pesticide of the class of N-phenylthioureas and photosensitiser to an average particle size 2 $\mu$m to 8 $\mu$m by homogeneously mixing and/or grinding said mixture with water-insoluble carriers and/or surface-active substances (surfactants), or by mixing the pesticide which has been preground to a granular size of 2 $\mu$m to 8 $\mu$m with the desired amount of photosensitiser. The photosensitiser may be used in the form of a crystalline solid as well as in the form of an aqueous solution. To prepare wettable powders it is preferred to use powdered photosensitiser, whereas suspension concentrates are prepared from aqueous solutions of the photosensitiser or powdered photosensitiser. A minor amount of water may be added to suspension concentrates (flowables) at this stage.

In addition to containing the photosensitiser, preferred compositions of this invention contain an insecticidally and acaricidally active N-phenylthiourea of formula I

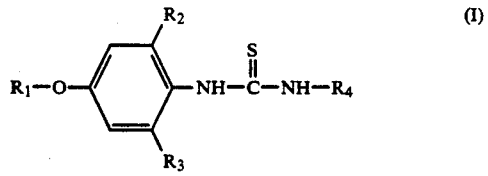

wherein
$R_1$ is phenyl, pyridyl, or phenyl or pyridyl each substituted by one or two members selected from the group consisting of $C_1$–$C_4$alkyl, trifluoromethyl or nitro
$R_2$ and $R_3$ are each independently of the other $C_1$–$C_4$alkyl, and
$R_4$ is $C_1$–$C_{10}$alkyl, $C_3$–$C_5$alkenyl, $C_3$–$C_6$cycloalkyl or $C_3$–$C_6$cycloalkyl-$C_1$–$C_4$alkyl.

Further preferred compositions are those in which $R_1$ is phenyl or phenyl which is monosubstituted by halogen, $C_1$–$C_4$alkyl or trifluoromethyl, and $R_2$, $R_3$ and $R_4$ are $C_1$–$C_4$alkyl.

Particularly preferred compositions are those which contain N-(2,6-diisopropyl-4-phenoxyphenyl)-N'-tert-butylthiourea as insecticide and acaricide.

Photosensitisers suitable for use in the compositions of this invention are compounds of the classes of the xanthene dyes such as Rose Bengal, thiazines such as Methylene Blue, porphyrins, thionines, eosines, erythrosines, phenosafranines, chlorophylls, flavines, thioxanthones, phthalocyanines, thiophenes, naphthalene derivatives, phenothiazines, pyrazolanthrones, ketocoumarins, azines such as riboflavines, anthraquinones, metallocenes, benzophenones and anthracene derivatives.

Preferred compositions of the invention contain photosensitisers of the classes of the xanthene dyes, thioxanthones, anthraquinones or phthalocyanines, in particular the preferred individual compounds:
disodium salt of 3',4',5',6'-tetrachloro-2,4,5,7-tetraiodofluoroescein, sodium salt of hydroxy- or chloroaluminium phthalocyaninesulfonic acid, sodium salt of 1-amino-4-bromoanthraquinone-2-sulfonic acid or nonaethylene glycol thioxanthone-1-carboxylate.

Combinations of N-phenylthiourea and photosensitiser which have been found particularly suitable are the combinations of compounds of formula I, especially those in which $R_1$ is phenyl or phenyl which is monosubstituted by halogen, $C_1$–$C_4$alkyl or trifluoromethyl, and $R_2$, $R_3$ and $R_4$ are $C_1$–$C_4$alkyl, with photosensitisers of the classes of the xanthene dyes, thioxanthones, anthraquinones or phthalocyanines.

Owing to the biological effect achieved, those compositions merit special mention which contain N-(2,6-diisopropyl-4-phenoxyphenyl)-N'-tert-butylthiourea as insecticide and acaricide and, as photosensitiser, disodium salt of 3',4',5',6'-tetrachloro-2,4,5,7-tetraiodofluoroscein or the sodium salt of hydroxyaluminiumphthalocyaninesulfonic acid, Commercial compositions of the preferred embodiment of the invention are normally formulated as wettable powders or suspension concentrates which contain, as pesticide, on the one hand 1 to 50% by weight of N-(2,6-diisopropyl-4-phenoxyphenyl)-N'-tert-butylthiourea having an average particle size of 2 $\mu$m to 8 $\mu$m, and, on the other, 0.1 to 10 mol % of disodium salt of 3',4',5',6'-tetrachloro-2,4,5,7-tetraiodofluoroescein, or of the sodium salt of hydroxyaluminiumphthalocyaninesulfonic acid, based on the amount of active thiourea.

The solid carriers used for dispersible powders and suspension concentrates are normally natural mineral fillers such as calcite, talcum, kaolin, montmorillonite or attapulgite. To improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Suitable surface-active compounds are non-ionic, cationic and/or anionic surfactants having good emulsifying, dispersing and wetting properties. The term "surfactants" will also be understood as comprising mixtures of surfactants. Suitable anionic surfactants can be water-soluble soaps as well as water-soluble synthetic surface-active compounds. Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tallow oil. Mention may also be made of fatty acid methyltaurin salts, as well as modified and unmodified phospholipids. More frequently, however, so-called synthetic surfactants are used, especially fatty sulfonates, fatty sulfates, sulfonated benzimidazole derivatives or alkylarylsulfonates. The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of ligninsulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical continint 8 to 22 carbon atoms. Examples of alkylsulfonates are the sodium, calcium or triethanolamine salts of dodecylbenzenesulfonic acid of dibutylnaphthalenesulfonic acid, or of a condensate of naphthalenesulfonic acid, and formaldehyde. Also suitable are corresponding phosphates, e.g. salts of the phosphated adduct of p-nonylphenol with 4 to 14 moles of ethylene oxide. Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic)hydrocarbon moiety and 6 to 18 carbon atoms in the alkyl moiety of the alkylphenols. Further suitable non-ionic surfactants are the water-soluble adducts of polyethylene oxide with polypropylene glycol, ethylenediaminopropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit. Representative examples of non-ionic surfactants are nonylphenol-polyethoxyethanols, castor oil polyglycol ethers, polypropylene/polyethylene oxide adducts, tributylphenoxypolyethyleneethanol, polyethylene glycol and octylphenoxypolyethoxyethanol. Fatty acid esters of polyoxyethylene sorbitan, e.g. polyoxyethalene sorbitan trioleate, are also suitable non-ionic surfactants. Cationic surfactants are preferably quaternary ammonium salts which contain, as N-substituent, at least one $C_8$–$C_{22}$alkyl radical and, as further substituents, unsubstituted or halogenated alkyl, benzyl or hydroxy-lower alkyl radicals. The salts are preferably in the form of halides, methylsulfates or ethylsulfates, e.g. stearyltrimethylammonium chloride or benzyl bis(2-chloroethyl)ethylammonium bromide.

The surfactants conventionally used in the art of formulation are described, for example, in the following publications:

"1985 International McCutcheon's Emulsifiers & Detergents", Glen Rock, NJ, USA, 1985", H. Stache, "Tensid-Taschenbuch" (Handbook of Surfactants), 2nd edition, C. Hanser Verlag Munich, Vienna 1981

M. and J. Ash, "Encyclopaedia of Surfactants", Vol. I-III, Chemical Publishing Co., New York, 1980-1981.

Particularly preferred compositions of this invention are formulated as follows (throughout, percentages are by weight):

| Suspension concentrates (Flowables) | |
|---|---|
| mixture of compound of formula I and photosensitiser: | 1 bis 75%, preferably 10 to 50% |
| water: | 24 to 98%, preferably 30 to 88% |
| surfactant: | 1 to 40%, preferably 2 to 30% |
| Wettable powder | |
| mixture of compound of formula I and photosensitiser: | 1 to 75%, preferably 10 to 50% |
| water: | 1 to 30%, preferably 10 to 85% |
| solids carrier: | 5 to 98%, preferably 25 to 80% |

The following Examples will serve to illustrate the invention, but imply no restriction to what is described therein.

BIOLOGICAL EXAMPLES

Example B1: Enhancement of Initial Action

Circular discs measuring 5 cm in diameter are cut from dwarf bean leaves in the 2-leaf stage (Autan variety). These discs are placed on a layer of moist cotton wool in petri dishes and each disc is populated with 10 adult females of the common spider mite (*Tetranychus urticae*). The infested leaf discs are sprayed with spray mixtures which contain the test compounds in the desired concentrations. The spray mixtures are prepared by adjusting the concentrations by diluting wettable powders or suspension concentrates with water and dissolving the desired amount of photosensitiser therein. The tests are evaluated 2, 4, 6 and 24 hours after application by making a mortality count of the treated pests. The tests are carried out at +26° C., at a relative humidity of 50-60%, and at a light intensity of 8000-10 000 lux.

| Test results: | |
|---|---|
| Test organism: | *Tetranychus urticae*, females, on dwarf bean leaf discs |
| Test substances: | compound 1a, granular sizes 3.8 μm and 7.1 μm |
| photosensitiser: | compound II |
| concentrations: | compound 1a: 400 ppm |
| | compound II: 1 mol % (ca. 10 ppm) |
| evaluation: | 2, 4, 6, 24 hours after application |

| Compound | Mortality in % after | | | |
|---|---|---|---|---|
| | 2 h | 4 h | 6 h | 24 h |
| compound 1a (3.8 μm) | 0 | 0 | 15 | 100 |
| compound 1a (3.8 μm) + compound II | 0 | 11 | 100 | 100 |
| compound 1a (7.1 μm) | 0 | 0 | 7 | 93 |
| compound 1a (7.1 μm) + compound II | 0 | 4 | 85 | 100 |

The addition of 1 mol % of photosensitiser of formula II reduces the time until onset of activity of compound 1a by ca. 18 hours.

Example B2: Enhancement of Activity at Reduced Concentrations

Circular discs measuring 5 cm in diameter are cut from dwarf bean leaves in the 2-leaf stage (Autan variety). These discs are placed on a layer of moist cotton wool in petri dishes and each disc is populated with adult females of the common spider mite (*Tetranychus*

*urticae*). The infested leaf discs are sprayed with spray mixtures which contain the test compounds of the class of the N-phenylthioureas in concentrations of 400, 200, 100, 50 and 25 ppm. The spray mixtures are prepared by diluting wettable powders or suspension concentrates with water and dissolving the indicated amount of photosensitiser therein. The tests are evaluated 24 hours after treatment by making a morality count of the pests. The tests are carried out at +26° C., at a relative humidity of 50-60%, and at a light intensity of 8000-10 000 lux.

Test results:

| | |
|---|---|
| test organism: | *Tetranychus urticae*, females, on dwarf bean leaf discs |
| test substances: | compound 1a, granular sizes 3.8 μm and 7.1 μm |
| photosensitisers: | compounds II, 3a, IV and V |
| concentrations: | compound 1a: 400, 200, 100, 50, 25 ppm |
| | compund II: 1 mol % |
| | compound 3a: 5 mol % |
| | compound IV: 5 mol % |
| | compound V: 5 mol % |
| evaluation: | 24 hours after application |

| Compound | Mortality in % at | | | | |
|---|---|---|---|---|---|
| | 400 ppm | 200 ppm | 100 ppm | 50 ppm | 25 ppm |
| compound 1a (3.8 μm) | 100 | 96 | 81 | 70 | 55 |
| compound 1a (3.8 μm) + compound II | 100 | 100 | 100 | 100 | 92 |
| compound 1a (3.8 μm) + compound 3a | 100 | 100 | 100 | 85 | 56 |
| compound 1a (3.8 μm) + compound IV | 100 | 100 | 100 | 86 | 55 |
| compound 1a (3.8 μm) + compound V | 100 | 100 | 100 | 100 | 100 |
| compound 1a (7.1 μm) | 93 | 46 | 26 | 0 | 0 |
| compound 1a (7.1 μm) + compound II | 100 | 100 | 100 | 36 | 0 |
| compound 1a (7.1 μm) + compound 3a | 100 | 100 | 100 | 50 | 20 |
| compound 1a (71 μm) + compound IV | 100 | 100 | 60 | 10 | 4 |
| compound 1a (71 μm) + compound V | 100 | 93 | 36 | 10 | 7 |

At low concentrations of compound of formula 1a, the addition of 1 to 5 mol % of photosensitiser markedly enhances the pesticidal activity.

Example B3: Prolongation of duration of activity

Dwarf bean plants in the 2-leaf stage (Autan variety) are sprayed with aqueous dispersions of the tested pesticidal N-phenylthioureas or with aqueous dispersions of the mixtures of the same N-phenylthioureas with the addition of photosensitiser. The spray mixtures contain the N-phenylthiourea in a concentration of 100 ppm. After the treatment, the spray coating is allowed to dry and the plants are cultivated in a greenhouse at +25° C., at a relative humidity of 50°-60° C. and under light for 14 hours per day. Then 1, 4, 8, 15 and 25 days after the spray treatment, two plants which have each been treated only with pesticide and with pesticide and photosensitiser are populated with a mixed population of the red spider mite (*Tetranychus cinnabarinus*). The test is evaluated 9 days after infestation by making a mortality count of the pests.

Test results:

| | |
|---|---|
| test organism: | *Tetranychus cinnabarinus*, mixed population on dwarf beans |
| test substances: | compound 1a, granular sizes 1.7 μm |
| photosensitiser: | compound 3a, |
| concentrations: | compound 1a: 100 ppm |
| | compound 3a: 2 mol % |
| population: | 1, 4, 8, 15, 25 days after spray treatment |
| evaluation: | 9 days after population |

| Population in days after spraying | Mortality in percent | |
|---|---|---|
| | compound 1a | compound 1a + 2 mol % compound 3a |
| 1 | 65 | 100 |
| 4 | 60 | 75 |
| 8 | 25 | 85 |
| 15 | 35 | 73 |
| 25 | 10 | 84 |

Old spray coatings of compound 1a have a markedly enhanced pesticidal activity when they contain 2 mol % of photosensitiser (compound 3a).

FORMULATION EXAMPLES

Example F1: Suspension concentrates (%=percent by weight)

| | |
|---|---|
| a) compound 1a | 40% |
| ethylene glycol | 10% |
| nonylphenol polyethylene glycol ether (15 mol EO) | 6% |
| sodium ligninsulfonate: | 10% |
| carboxymethyl cellulose | 1% |
| 37% aqueous formaldehyde solution: | 0.2% |
| silicone oil (75% emulsion) | 0.8% |
| water | 32% |
| b) compound 1a | 49.87% |
| photosensitiser II | 0.13% |
| ethylene glycol | 10% |
| nonylphenol polyethylene glycol ether (15 mol EO) | 6% |
| sodium ligninsulfonate | 10% |
| carboxymethyl cellulose | 1% |
| 37% aqueous formaldehyde solution | 0.2% |
| silicone oil (75% emulsion) | 0.8% |
| water | 22% |
| c) compound 1a | 49.87% |
| photosensitiser II | 1.29% |
| ethylene glycol | 10% |
| nonylphenol polyethylene glycol ether (15 mol EO) | 6% |
| sodium ligninsulfonate | 10% |
| carboxymethyl cellulose | 1% |
| 37% aqueous formaldehyde solution | 0.2% |
| silicone oil (75% emulsion) | 0.8% |
| water | 22% |
| d) compound 1a | 44.15% |
| photosensitiser II | 5.85% |
| ethylene glycol | 10% |
| nonylphenol polyethylene glycol ether (15 mol EO) | 6% |
| sodium ligninsulfonate | 10% |
| carboxymethyl cellulose | 1% |
| 37% aqueous formaldehyde solution | 0.2% |
| silicone oil (75% emulsion) | 0.8% |
| water | 22% |
| e) compound 1a | 39.54% |
| photosensitiser II | 10.46% |
| ethylene glycol | 10% |
| nonylphenol polyethylene glycol ether (15 mol EO) | 6% |
| sodium ligninsulfonate | 10% |
| carboxymethyl cellulose | 1% |
| 37% aqueous formaldehyde solution | 0.2% |
| silicone oil (75% emulsion) | 0.8% |
| water | 22% |
| f) compound 1a | 49.88% |
| photosensitiser 3a | 0.12% |
| ethylene glycol | 10% |
| nonylphenol polyethylene glycol ether (15 mol EO) | 6% |

| | |
|---|---|
| sodium ligninsulfonate | 10% |
| carboxymethyl cellulose | 1% |
| 37% aqueous formaldehyde solution | 0.2% |
| silicone oil (75% emulsion) | 0.8% |
| water | 22% |
| g) compound 1a | 48.84% |
| photosensitiser 3a | 1.16% |
| ethylene glycol | 10% |
| nonylphenol polyethylene glycol ether (15 mol EO) | 6% |
| sodium ligninsulfonate | 10% |
| carboxymethyl cellulose | 1% |
| 37% aqueous formaldehyde solution | 0.2% |
| silicone oil (75% emulsion) | 0.8% |
| water | 22% |
| h) compound 1a | 44.70% |
| photosensitiser 3a | 5.30% |
| ethylene glycol | 10% |
| nonylphenol polyethylene glycol ether (15 mol EO) | 6% |
| sodium ligninsulfonate | 10% |
| carboxymethyl cellulose | 1% |
| 37% aqueous formaldehyde solution | 0.2% |
| silicone oil (75% emulsion) | 0.8% |
| water | 22% |
| i) compound 1a | 40.41% |
| photosensitiser 3a | 9.59% |
| ethylene glycol | 10% |
| nonylphenol polyethylene glycol ether (15 mol EO) | 6% |
| sodium ligninsulfonate | 10% |
| carboxymethyl cellulose | 1% |
| 37% aqueous formaldehyde solution | 0.2% |
| silicone oil (75% emulsion) | 0.8% |
| water | 22% |
| j) compound 1a | 47.50% |
| photosensitiser V | 2.50% |
| ethylene glycol | 10% |
| nonylphenol polyethylene glycol ether (15 mol EO) | 5% |
| sodium ligninsulfonate | 11% |
| carboxymethyl cellulose | 1% |
| 37% aqueous formaldehyde solution | 0.2% |
| silicone oil (75% emulsion) | 0.8% |
| water | 22% |
| k) compound 1a | 45% |
| photosensitiser V | 5% |
| ethylene glycol | 8% |
| nonylphenol polyethylene glycol ether (15 mol EO) | 6% |
| sodium ligninsulfonate | 10% |
| carboxymethyl cellulose | 1% |
| 37% aqueous formaldehyde solution | 0.2% |
| silicone oil (75% emulsion) | 0.8% |
| water | 22% |
| l) compound 1a | 50% |
| ethylene glycol | 8% |
| nonylphenol polyethylene glycol ether (15 mol EO) | 6% |
| sodium ligninsulfonate | 8% |
| carboxymethyl cellulose | 1% |
| 37% aqueous formaldehyde solution | 0.3% |
| silicone oil (75% emulsion) | 0.7% |
| water | 26% |
| m) compound 1a | 50% |
| ethylene glycol | 10% |
| nonylphenol polyethylene glycol ether (15 mol EO) | 6% |
| sodium ligninsulfonate | 10% |
| carboxymethyl cellulose | 1% |
| 37% aqueous formaldehyde solution | 0.2% |
| silicone oil (75% emulsion) | 0.8% |
| water | 22% |
| n) compound 1a | 49.35% |
| photosensitiser II | 0.65% |
| ethylene glycol | 10% |
| nonylphenol polyethylene glycol ether (15 mol EO) | 6% |
| sodium ligninsulfonate | 10% |
| carboxymethyl cellulose | 1% |
| 37% aqueous formaldehyde solution | 0.2% |
| silicone oil (75% emulsion) | 0.8% |
| water | 22% |
| o) compound 1a | 47.42% |
| photosensitiser II | 2.58% |
| ethylene glycol | 10% |
| nonylphenol polyethylene glycol ether (15 mol EO) | 6% |
| sodium ligninsulfonate | 10% |
| carboxymethyl cellulose | 1% |
| 37% aqueous formaldehyde solution | 0.2% |
| silicone oil (75% emulsion) | 0.8% |
| water | 22% |
| p) compound 1a | 49.37% |
| photosensitiser 3a | 0.63% |
| ethylene glycol | 10% |
| nonylphenol polyethylene glycol ether (15 mol EO) | 6% |
| sodium ligninsulfonate | 10% |
| carboxymethyl cellulose | 1% |
| 37% aqueous formaldehyde solution | 0.2% |
| silicone oil (75% emulsion) | 0.8% |
| water | 22% |
| q) compound 1a | 47.54% |
| photosensitiser 3a | 2.46% |
| ethylene glycol | 10% |
| nonylphenol polyethylene glycol ether (15 mol EO) | 6% |
| sodium ligninsulfonate | 10% |
| carboxymethyl cellulose | 1% |
| 37% aqueous formaldehyde solution | 0.2% |
| silicone oil (75% emulsion) | 0.8% |
| water | 22% |
| r) compound 1a | 50% |
| 1,2-propylene glycol | 5% |
| ethylene glycol | 0.32% |
| silicone oil (30% emulsion) | 0.5% |
| mixture of the phosphated triethanol-ammonium salt of mono- and di(tristyryl-phenolpolyglycol ether) (18 mol EO) | 1.2% |
| polysaccharide | 0.1% |
| 37% aqueous formaldehyde solution | 0.1% |
| water | 42.78% |
| s) compound 1a | 49.87% |
| photosensitiser II | 0.13% |
| 1,2-propylene glycol | 5% |
| ethylene glycol | 0.32% |
| silicone oil (30% emulsion) | 0.5% |
| mixture of the phosphated triethanol-ammonium salt of mono- and di(tristyryl-phenolpolyglycol ether) (18 mol EO) | 1.2% |
| polysaccharide | 0.1% |
| 37% aqueous formaldehyde solution | 0.1% |
| water | 42.78% |
| t) compound 1a | 49.35% |
| photosensitiser II | 0.65% |
| 1,2-propylene glycol | 5% |
| ethylene glycol | 0.32% |
| silicone oil (30% emulsion) | 0.5% |
| mixture of the phosphated triethanol-ammonium salt of mono- and di(tristyryl-phenolpolyglycol ether) (18 mol EO) | 1.2% |
| polysaccharide | 0.1% |
| 37% aqueous formaldehyde solution | 0.1% |
| water | 42.78% |
| u) compound 1a | 48.71% |
| photosensitiser II | 1.29% |
| 1,2-propylene glycol | 5% |
| ethylene glycol | 0.32% |
| silicone oil (30% emulsion) | 0.5% |
| mixture of the phosphated triethanol-ammonium salt of mono- and di(tristyryl-phenolpolyglycol ether) (18 mol EO) | 1.2% |
| polysaccharide | 0.1% |
| 37% aqueous formaldehyde solution | 0.1% |
| water | 42.78% |
| v) compound 1a | 47.42% |
| photosensitiser II | 2.58% |
| 1,2-propylene glycol | 5% |
| ethylene glycol | 0.32% |

-continued

| | |
|---|---|
| silicone oil (30% emulsion) | 0.5% |
| mixture of the phosphated triethanol-ammonium salt of mono- and di(tristyryl-phenolpolyglycol ether) (18 mol EO) | 1.2% |
| polysaccharide | 0.1% |
| 37% aqueous formaldehyde solution | 0.1% |
| water | 42.78% |
| w) compound 1a | 44.15% |
| photosensitiser II | 5.85% |
| 1,2-propylene glycol | 5% |
| ethylene glycol | 0.32% |
| silicone oil (30% emulsion) | 0.5% |
| mixture of the phosphated triethanol-ammonium salt of mono- and di(tristyryl-phenolpolyglycol ether) (18 mol EO) | 1.2% |
| polysaccharide | 0.1% |
| 37% aqueous formaldehyde solution | 0.1% |
| water | 42.78% |
| x) compound 1a | 49.87% |
| photosensitiser 3a | 0.13% |
| 1,2-propylene glycol | 5% |
| ethylene glycol | 0.32% |
| silicone oil (30% emulsion) | 0.5% |
| mixture of the phosphated triethanol-ammonium salt of mono- and di(tristyryl-phenolpolyglycol ether) (18 mol EO) | 1.2% |
| polysaccharide | 0.1% |
| 37% aqueous formaldehyde solution | 0.1% |
| water | 42.78% |
| y) compound 1a | 48.75% |
| photosensitiser 3a | 1.25% |
| 1,2-propylene glycol | 5% |
| ethylene glycol | 0.32% |
| silicone oil (30% emulsion) | 0.5% |
| mixture of the phosphated triethanol-ammonium salt of mono- and di(tristyryl-phenolpolyglycol ether) (18 mol EO) | 1.2% |
| polysaccharide | 0.1% |
| 37% aqueous formaldehyde solution | 0.1% |
| water | 42.78% |
| z) compound 1a | 49.37% |
| photosensitiser II | 0.63% |
| 1,2-propylene glycol | 5% |
| ethylene glycol | 0.32% |
| silicone oil (30% emulsion) | 0.5% |
| mixture of the phosphated triethanol-ammonium salt of mono- and di(tristyryl-phenolpolyglycol ether) (18 mol EO) | 1.2% |
| polysaccharide | 0.1% |
| 37% aqueous formaldehyde solution | 0.1% |
| water | 42.78% |
| aa) compound 1a | 47.54% |
| photosensitiser II | 2.46% |
| 1,2-propylene glycol | 5% |
| ethylene glycol | 0.32% |
| silicone oil (30% emulsion) | 0.5% |
| mixture of the phosphated triethanol-ammonium salt of mono- and di(tristyryl-phenolpolyglycol ether) (18 mol EO) | 1.2% |
| polysaccharide | 0.1% |
| 37% aqueous formaldehyde solution | 0.1% |
| water | 42.78% |
| bb) compound 1a | 44.3% |
| photosensitiser II | 5.7% |
| 1,2-propylene glycol | 5% |
| ethylene glycol | 0.32% |
| silicone oil (30% emulsion) | 0.5% |
| mixture of the phosphated triethanol-ammonium salt of mono- and di(tristyryl-phenolpolyglycol ether) (18 mol EO) | 1.2% |
| polysaccharide | 0.1% |
| 37% aqueous formaldehyde solution | 0.1% |
| water | 42.78% |

Example F2: Wettable powders (% = percent by weight)

| | |
|---|---|
| a) compound 1a | 50% |
| 1-benzyl-2-heptadecyl-benzimidazoledisulfonic acid, sodium salt | 8% |
| sodium lauryl sulfate | 2% |
| highly dispersed silicic acid | 3% |
| kaolin | 37% |
| b) compound 1a | 50% |
| sodium dibutylnaphthalenesulfonate | 13% |
| octylphenol polyethylene glycol ether (8 mol EO) | 5% |
| urea/formaldehyde condensation polymer | 5% |
| highly dispersed silicic acid | 5% |
| kaolin | 22% |
| c) compound 1a | 49.87% |
| photosensitiser II | 0.13% |
| 1-benzyl-2-heptadecyl-benzimidazoledisulfonic acid, sodium salt | 8% |
| sodium lauryl sulfate | 2% |
| highly dispersed silicic acid | 3% |
| kaolin | 37% |
| d) compound 1a | 49.87% |
| photosensitiser II | 0.13% |
| sodium dibutylnaphthalenesulfonate | 13% |
| octylphenol polyethylene glycol ether (8 mol EO) | 5% |
| urea/formaldehyde condensation polymer | 5% |
| highly dispersed silicic acid | 5% |
| kaolin | 22% |
| e) compound 1a | 48.71% |
| photosensitiser II | 1.29% |
| 1-benzyl-2-heptadecyl-benzimidazoledisulfonic acid, sodium salt | 8% |
| sodium lauryl sulfate | 2% |
| highly dispersed silicic acid | 3% |
| kaolin | 37% |
| f) compound 1a | 48.71% |
| photosensitiser II | 1.29% |
| sodium dibutylnaphthalenesulfonate | 13% |
| octylphenol polyethylene glycol ether (8 mol EO) | 5% |
| urea/formaldehyde condensation polymer | 5% |
| highly dispersed silicic acid | 5% |
| kaolin | 22% |
| g) compound 1a | 44.15% |
| photosensitiser II | 5.85% |
| 1-benzyl-2-heptadecyl-benzimidazoledisulfonic acid, sodium salt | 8% |
| sodium lauryl sulfate | 2% |
| highly dispersed silicic acid | 3% |
| kaolin | 37% |
| h) compound 1a | 44.15% |
| photosensitiser II | 5.85% |
| sodium dibutylnaphthalenesulfonate | 13% |
| octylphenol polyethylene glycol ether (8 mol EO) | 5% |
| urea/formaldehyde condensation polymer | 5% |
| highly dispersed silicic acid | 5% |
| kaolin | 22% |
| i) compound 1a | 39.54% |
| photosensitiser II | 10.46% |
| 1-benzyl-2-heptadecyl-benzimidazoledisulfonic acid, sodium salt | 8% |
| sodium lauryl sulfate | 2% |
| highly dispersed silicic acid | 3% |
| kaolin | 37% |
| j) compound 1a | 39.54% |
| photosensitiser II | 10.46% |
| sodium dibutylnaphthalenesulfonate | 13% |
| octylphenol polyethylene glycol ether (8 mol EO) | 5% |
| urea/formaldehyde condensation polymer | 5% |
| highly dispersed silicic acid | 5% |
| kaolin | 22% |
| k) compound 1a | 49.88% |
| photosensitiser 3a | 0.12% |
| 1-benzyl-2-heptadecyl-benzimidazoledisulfonic acid, sodium salt | 8% |
| sodium lauryl sulfate | 2% |
| highly dispersed silicic acid | 3% |
| kaolin | 37% |
| l) compound 1a | 49.88% |
| photosensitiser 3a | 0.12% |
| sodium dibutylnaphthalenesulfonate | 13% |
| octylphenol polyethylene glycol ether | 5% |

-continued

| | |
|---|---|
| (8 mol EO) | |
| urea/formaldehyde condensation polymer | 5% |
| highly dispersed silicic acid | 5% |
| kaolin | 22% |
| m) compound 1a | 48.84% |
| photosensitiser 3a | 1.16% |
| 1-benzyl-2-heptadecyl-benzimidazoledisulfonic acid, sodium salt | 8% |
| sodium lauryl sulfate | 2% |
| highly dispersed silicic acid | 3% |
| kaolin | 37% |
| n) compound 1a | 48.84% |
| photosensitiser 3a | 1.16% |
| sodium dibutylnaphthalenesulfonate | 13% |
| octylphenol polyethylene glycol ether (8 mol EO) | 5% |
| urea/formaldehyde condensation polymer | 5% |
| highly dispersed silicic acid | 5% |
| kaolin | 22% |
| o) compound 1a | 44.70% |
| photosensitiser 3a | 5.30% |
| 1-benzyl-2-heptadecyl-benzimidazoledisulfonic acid, sodium salt | 8% |
| sodium lauryl sulfate | 2% |
| highly dispersed silicic acid | 3% |
| kaolin | 37% |
| p) compound 1a | 44.70% |
| photosensitiser 3a | 5.30% |
| sodium dibutylnaphthalenesulfonate | 13% |
| octylphenol polyethylene glycol ether (8 mol EO) | 5% |
| urea/formaldehyde condensation polymer | 5% |
| highly dispersed silicic acid | 5% |
| kaolin | 22% |
| q) compound 1a | 49.87% |
| photosensitiser 3a | 9.59% |
| 1-benzyl-2-heptadecyl-benzimidazoledisulfonic acid, sodium salt | 8% |
| sodium lauryl sulfate | 2% |
| highly dispersed silicic acid | 3% |
| kaolin | 37% |
| r) compound 1a | 40.41% |
| photosensitiser 3a | 9.59% |
| sodium dibutylnaphthalenesulfonate | 13% |
| octylphenol polyethylene glycol ether (8 mol EO) | 5% |
| urea/formaldehyde condensation polymer | 5% |
| highly dispersed silicic acid | 5% |
| kaolin | 22% |
| s) compound 1a | 49.95% |
| photosensitiser IV | 0.05% |
| 1-benzyl-2-heptadecyl-benzimidazoledisulfonic acid, sodium salt | 8% |
| sodium lauryl sulfate | 2% |
| highly dispersed silicic acid | 3% |
| kaolin | 37% |
| t) compound 1a | 49.95% |
| photosensitiser IV | 0.05% |
| sodium dibutylnaphthalenesulfonate | 13% |
| octylphenol polyethylene glycol ether (8 mol EO) | 5% |
| urea/formaldehyde condensation polymer | 5% |
| highly dispersed silicic acid | 5% |
| kaolin | 22% |
| u) compound 1a | 49.50% |
| photosensitiser IV | 0.50% |
| 1-benzyl-2-heptadecyl-benzimidazoledisulfonic acid, sodium salt | 8% |
| sodium lauryl sulfate | 2% |
| highly dispersed silicic acid | 3% |
| kaolin | 37% |
| v) compound 1a | 49.50% |
| photosensitiser IV | 0.50% |
| sodium dibutylnaphthalenesulfonate | 13% |
| octylphenol polyethylene glycol ether (8 mol EO) | 5% |
| urea/formaldehyde condensation polymer | 5% |
| highly dispersed silicic acid | 5% |
| kaolin | 22% |
| w) compound 1a | 47.50% |
| photosensitiser IV | 2.50% |
| 1-benzyl-2-heptadecyl-benzimidazoledisulfonic acid, sodium salt | 8% |
| sodium lauryl sulfate | 2% |
| highly dispersed silicic acid | 3% |
| kaolin | 37% |
| x) compound 1a | 47.50% |
| photosensitiser IV | 2.50% |
| sodium dibutylnaphthalenesulfonate | 13% |
| octylphenol polyethylene glycol ether (8 mol EO) | 5% |
| urea/formaldehyde condensation polymer | 5% |
| highly dispersed silicic acid | 5% |
| kaolin | 22% |
| y) compound 1a | 45% |
| photosensitiser IV | 5% |
| 1-benzyl-2-heptadecyl-benzimidazoledisulfonic acid, sodium salt | 8% |
| sodium lauryl sulfate | 2% |
| highly dispersed silicic acid | 3% |
| kaolin | 37% |
| z) compound 1a | 45% |
| photosensitiser IV | 5% |
| sodium dibutylnaphthalenesulfonate | 13% |
| octylphenol polyethylene glycol ether (8 mol EO) | 5% |
| urea/formaldehyde condensation polymer | 5% |
| highly dispersed silicic acid | 5% |
| kaolin | 22% |
| aa) compound 1a | 47.42% |
| photosensitiser II | 2.58% |
| 1-benzyl-2-heptadecyl-benzimidazoledisulfonic acid, sodium salt | 8% |
| sodium lauryl sulfate | 2% |
| highly dispersed silicic acid | 3% |
| kaolin | 37% |
| bb) compound 1a | 47.42% |
| photosensitiser II | 2.58% |
| sodium dibutylnaphthalenesulfonate | 13% |
| octylphenol polyethylene glycol ether (8 mol EO) | 5% |
| urea/formaldehyde condensation polymer | 5% |
| highly dispersed silicic acid | 5% |
| kaolin | 22% |
| cc) compound 1a | 49.35% |
| photosensitiser II | 0.65% |
| 1-benzyl-2-heptadecyl-benzimidazoledisulfonic acid, sodium salt | 8% |
| sodium lauryl sulfate | 2% |
| highly dispersed silicic acid | 3% |
| kaolin | 37% |
| dd) compound 1a | 49.35% |
| photosensitiser II | 0.65% |
| sodium dibutylnaphthalenesulfonate | 13% |
| octylphenol polyethylene glycol ether (8 mol EO) | 5% |
| urea/formaldehyde condensation polymer | 5% |
| highly dispersed silicic acid | 5% |
| kaolin | 22% |
| ee) compound 1a | 49.37% |
| photosensitiser 3a | 0.63% |
| 1-benzyl-2-heptadecyl-benzimidazoledisulfonic acid, sodium salt | 8% |
| sodium lauryl sulfate | 2% |
| highly dispersed silicic acid | 3% |
| kaolin | 37% |
| ff) compound 1a | 49.37% |
| photosensitiser 3a | 0.63% |
| sodium dibutylnaphthalenesulfonate | 13% |
| octylphenol polyethylene glycol ether (8 mol EO) | 5% |
| urea/formaldehyde condensation polymer | 5% |
| highly dispersed silicic acid | 5% |
| kaolin | 22% |
| gg) compound 1a | 47.54% |
| photosensitiser 3a | 2.46% |
| 1-benzyl-2-heptadecyl-benzimidazoledisulfonic acid, sodium salt | 8% |

-continued

| | |
|---|---|
| sodium lauryl sulfate | 2% |
| highly dispersed silicic acid | 3% |
| kaolin | 37% |
| hh) compound 1a | 47.54% |
| photosensitiser 3a | 2.46% |
| sodium dibutylnaphthalenesulfonate | 13% |
| octylphenol polyethylene glycol ether (8 mol EO) | 5% |
| urea/formaldehyde condensation polymer | 5% |
| highly dispersed silicic acid | 5% |
| kaolin | 22% |

What is claimed is:

1. An insecticidal and acaricidal composition, having enhanced activity, which contains an effective amount of an insecticidally and acaricidally active N-phenylthiourea of the formula

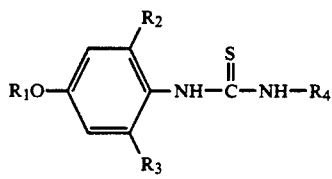

wherein
R$_1$ is phenyl or phenyl substituted by one or two substituents selected from the group consisting of chlorine, C$_1$–C$_4$alkyl, trifluoromethyl or nitro, R$_2$ and R$_3$ are each independently of the other C$_1$–C$_4$alkyl, and R$_4$ is C$_1$–C$_{10}$alkyl, C$_3$–C$_5$alkenyl, C$_3$–C$_6$cycloalkyl or C$_3$–C$_6$cycloalkyl-C$_1$–C$_4$alkyl,
and a synergistically effective amount of a photosensitizer selected from the group consisting of the disodium salt of 3',4',5',6'-tetrachloro-2,4,5,7-tetraiodofluoroescein and the sodium salt of hydroxyaluminum phthalocyaninesulfonic acid, together with an inert carrier.

2. The composition of claim 1, wherein R$_1$ is phenyl or phenyl which is monosubstituted by halogen, alkyl or trifluoromethyl, and R$_2$, R$_3$ and R$_4$ are C$_1$–C$_4$alkyl.

3. The composition of claim 1, wherein the N-phenylthiourea is N-(2,6-diisopropyl-4-phenoxyphenyl)-N'-tert-butylthiourea.

4. The composition of claim 1, wherein the N-phenylthiourea is N-(2,6-diisopropyl-4-phenoxyphenyl)-N'-tert-butylthiourea and the photosensitizer is the disodium salt of 3',4',5',6'-tetrachloro-2,4,5,7-tetraiodofluoroescein.

5. The composition of claim 1, wherein the N-phenylthiourea is N-(2,6-diisopropyl-4-phenoxyphenyl)-N'-tert-butylthiourea and the photosensitizer is the sodium salt of hydroxyaluminum phthalocyaninesulfonic acid.

6. The composition of claim 1 which is in the form of a wettable powder or suspension concentrate.

7. The composition of claim 1 which is in the form of a wettable powder or suspension concentrate comprising 1 to 50% by weight of N-(2,6-diisopropyl-4-phenoxyphenyl)-N'-tert-butylthiourea having an average particle size of 2 μm to 8 μm, and 0.1 to 10 mol % of the disodium salt of 3',4',5',6'-tetrachloro-2,4,5,7-tetraiodofluoroescein or the sodium salt of hydroxyaluminum phthalocyaninesulfonic acid, based on the amount of active thourea.

8. The composition of claim 1, which is in the form of a wettable powder comprising 48.71% of N-(2,6-diisopropyl-4-phenoxyphenyl)-N'-tert-butylthiourea, 1.29% of the disodium salt of 3',4',5',6'-tetrachloro-2,4,5,7-tetraiodofluoroescein, 13% of sodium dibutylnaphthalenesulfonate, 5% of octylphenol polyethylene glycol (8 mol EO), 5% of ground urea/formaldehyde condensation polymer, 5% of highly dispersed silicic acid and 22% of kaolin.

9. The composition of claim 1 which is in the form of a wettable powder comprising 44.70% of N-(2,6-diisopropyl-4-phenoxyphenyl)-N'-tert-butylthiourea, 5.30% of the sodium salt of hydroxy-aluminum phthalocyaninesulfonic acid, 13% of sodium dibutylnaphthalenesulfonate, 5% of octylphenol polyethylene glycol (8 mol EO), 5% of ground urea/formaldehyde condensation polymer, 5% of highly dispersed silicic acid and 22% of kaolin.

10. The composition of claim 1 which is in the form of a suspension concentrate comprising 47.54% of N-(2,6-diisopropyl-4-phenoxyphenyl)-N'-tert-butylthiourea, 5.30% of the sodium salt of hydroxyaluminum phthalocyaninesulfonic acid, 5% of 1,2-propylene glycol, 0.32% of ethylene glycol, 0.5% of a 30% emulsion of silicone oil, 1.2% of a mixture of the phosphated triethanolammonium salt of mono- and di(tristyrylphenolpolyglycol ether) (18 mol EO), 0.1% of polysaccharide, 0.1% of a 37% aqueous solution of formaldehyde, and 42.78% of water.

11. A method of controlling pests, selected from the group consisting of insects and members of the order Acarina, which comprises the step of applying to said pests or habitat thereof a synergistic insecticidally and acaricidally effective amount of a composition which contains an effective amount of an insecticidally and acaricidally active N-phenylthiourea of the formula

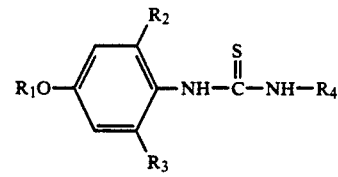

wherein
R$_1$ is phenyl or phenyl substituted by one or two substituents selected from the group consisting of chlorine, C$_1$–C$_4$alkyl, trifluoromethyl or nitro, R$_2$ and R$_3$ are each independently of the other C$_1$–C$_4$alkyl, and R$_4$ is C$_1$–C$_{10}$alkyl, C$_3$–C$_5$alkenyl, C$_3$–C$_6$cycloalkyl or C$_3$–C$_6$cycloalkyl-C$_1$–C$_4$alkyl,
and a synergistically effective amount of a photosensitizer selected from the group consisting of the disodium salt of 3',4',5',6'-tetrachloro-2,4,5,7-tetraiodofluoroescein and the sodium salt of hydroxyaluminum phthalocyaninesulfonic acid, together with an inert carrier.

12. The method of claim 11, wherein 0.01 to 50 mol % of the photosensitizer is applied, based on the N-phenylthiourea.

13. The method of claim 11, wherein the N-phenylthiourea is applied to the locus of treatment in a concentration in the range of 0.1 to 1000 ppm and wherein the locus of treatment is a cultivated plant or the cultivated area of said plant.

* * * * *